(12) United States Patent
Clark et al.

(10) Patent No.: US 7,038,219 B2
(45) Date of Patent: *May 2, 2006

(54) STERILIZATION OF PACKAGES AND THEIR CONTENTS USING LIGHT

(75) Inventors: Reginald Wayne Clark, Del Mar, CA (US); James C. Lierman, San Diego, CA (US); Donald Lander, La Jolla, CA (US); Joseph E. Dunn, Crystal Lake, IL (US)

(73) Assignee: PurePulse Technologies, Inc., San Diego, CA (US)

( * ) Notice: Subject to any disclaimer, the term of this patent is extended or adjusted under 35 U.S.C. 154(b) by 558 days.

This patent is subject to a terminal disclaimer.

(21) Appl. No.: 10/039,311

(22) Filed: Oct. 26, 2001

(65) Prior Publication Data

US 2003/0155531 A1 Aug. 21, 2003

(Under 37 CFR 1.47)

Related U.S. Application Data

(63) Continuation of application No. 09/326,168, filed on Jun. 4, 1999, now Pat. No. 6,566,659, which is a continuation-in-part of application No. 08/846,102, filed on May 1, 1997, now Pat. No. 5,925,885, which is a continuation-in-part of application No. 08/651,275, filed on May 22, 1996, now Pat. No. 5,786,598.

(51) Int. Cl.
*A61L 2/10* (2006.01)
*B65B 55/08* (2006.01)

(52) U.S. Cl. ..................... 250/455.11; 422/24
(58) Field of Classification Search ............ 250/453.11, 250/454.11, 455.11, 491.1, 492.1; 422/24; 137/7, 42

See application file for complete search history.

(56) References Cited

U.S. PATENT DOCUMENTS

| | | | |
|---|---|---|---|
| 4,063,890 A | | 12/1977 | Baron |
| 4,282,863 A | | 8/1981 | Beigler et al. |
| 4,304,996 A | | 12/1981 | Blades |
| 4,464,336 A | | 8/1984 | Hiramoto |
| 4,469,835 A | | 9/1984 | Laurin |
| 4,540,416 A | | 9/1985 | Hattori et al. |
| 4,629,658 A | | 12/1986 | Lucas |
| 4,657,540 A | | 4/1987 | Iwamoto et al. |
| 4,866,282 A | | 9/1989 | Miripol et al. |
| 4,868,397 A | * | 9/1989 | Tittel .................. 250/455.11 |
| 4,871,559 A | | 10/1989 | Dunn et al. |
| 5,017,238 A | * | 5/1991 | Chromecek et al. .......... 134/7 |

(Continued)

FOREIGN PATENT DOCUMENTS

| | | |
|---|---|---|
| EP | 1033138 | 6/2000 |
| GB | 2141723 | 1/1985 |
| GB | 2117733 | 10/1993 |
| WO | WO-8201703 | 5/1982 |
| WO | WO-8803369 | 5/1988 |
| WO | WO-9516565 | 6/1995 |
| WO | WO 96/05869 A1 | 2/1996 |

OTHER PUBLICATIONS

Dunn, et al.; "Pulsed Light Treatment of Food and Packaging", *Food Technology*, vol. 49:9, pp 95–98 (Sep. 1995).

Primary Examiner—John R. Lee
Assistant Examiner—David A. Vanore
(74) Attorney, Agent, or Firm—Thomas F. Lebens; Fitch, Even, Tabin & Flannery

(57) ABSTRACT

An apparatus, and related methods for sterilizing microorganisms in a container, the apparatus consists of the container including a blister formed therein and a backing material that together with the blister form a cavity in which is contained a contact lens and a preservative fluid. A flashlamp generates high-intensity, short-duration pulses of light for deactivating microorganisms within the container by illuminating the container with the pulses of light having been generated.

37 Claims, 5 Drawing Sheets

U.S. PATENT DOCUMENTS

| | | | | |
|---|---|---|---|---|
| 5,037,484 A | * | 8/1991 | Su et al. | 134/7 |
| 5,038,336 A | * | 8/1991 | Kitazawa | 369/71 |
| 5,122,126 A | | 6/1992 | Sakakiyama | |
| 5,129,894 A | | 7/1992 | Sommermeyer et al. | |
| 5,144,144 A | * | 9/1992 | Borovsky | 250/455.11 |
| 5,166,528 A | * | 11/1992 | Le Vay | 250/455.11 |
| 5,324,233 A | | 6/1994 | Owensby et al. | |
| 5,494,155 A | | 2/1996 | Evans et al. | |
| 5,643,464 A | | 7/1997 | Rhee et al. | |
| 5,658,530 A | * | 8/1997 | Dunn | 422/24 |
| 5,768,853 A | | 6/1998 | Bushnell et al. | |
| 5,786,598 A | * | 7/1998 | Clark et al. | 250/455.11 |
| 5,900,211 A | * | 5/1999 | Dunn et al. | 422/24 |
| 5,925,885 A | | 7/1999 | Clark et al. | |
| 6,028,830 A | * | 2/2000 | Fritsch et al. | 369/71 |
| 6,080,361 A | * | 6/2000 | Borovsky | 422/1 |
| 6,099,522 A | | 8/2000 | Knopp et al. | |
| 6,565,803 B1 | * | 5/2003 | Bolton et al. | 422/24 |
| 6,566,659 B1 | * | 5/2003 | Clark et al. | 250/455.11 |
| 6,649,722 B1 | * | 11/2003 | Rosenzweig et al. | 526/279 |
| 2003/0080467 A1 | * | 5/2003 | Andrews et al. | 264/275 |

* cited by examiner

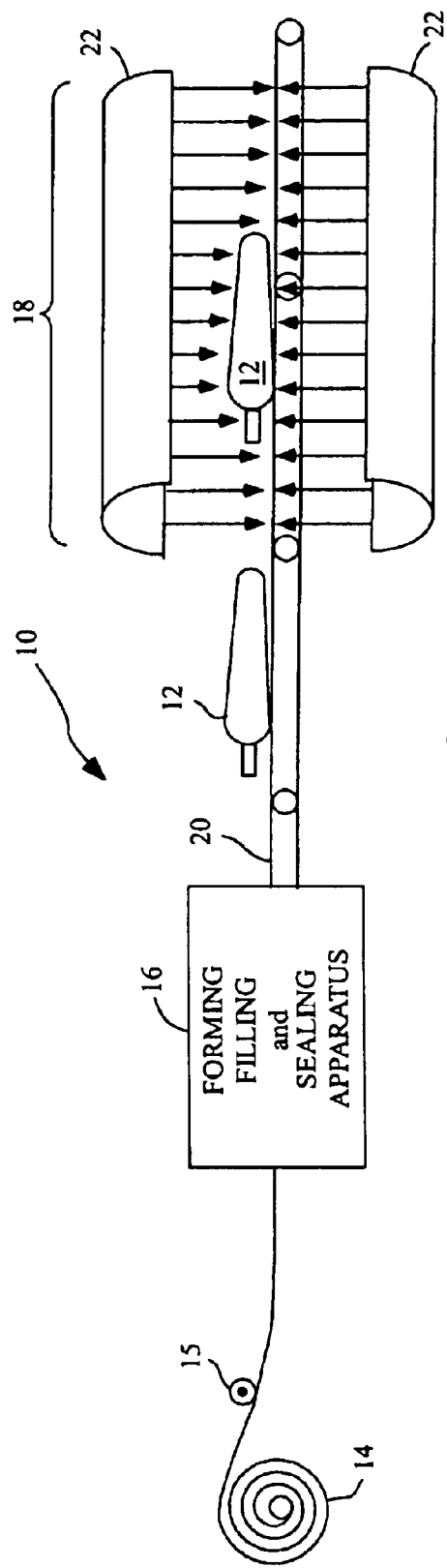
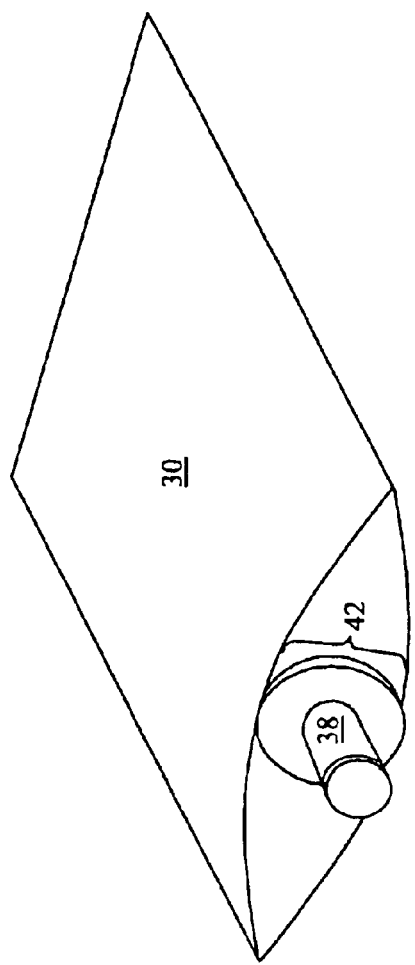
Fig.3
Fig.5
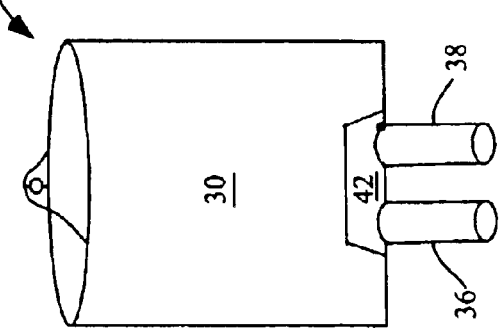
Fig.4

STERILIZATION OF PACKAGES AND THEIR CONTENTS USING LIGHT

This application is a continuation of U.S. application Ser. No. 09/326,168, filed Jun. 4, 1999, entitled PARAMETRIC CONTROL IN PULSED LIGHT STERILIZATION, now U.S. Pat. No. 6,566,659, which is a continuation-in-part (CIP) of U.S. application Ser. No. 08/846,102, filed May 1, 1997, entitled PARAMETRIC CONTROL IN PULSED LIGHT STERILIZATION OF PACKAGES AND THEIR CONTENTS, now U.S. Pat. No. 5,925,885, which is a CIP of U.S. application Ser. No. 08/651,275, filed May 22, 1996, entitled STERILIZATION OF PACKAGES AND THEIR CONTENTS USING HIGH-INTENSITY, SHORT-DURATION PULSES OF INCOHERENT, POLYCHROMATIC LIGHT IN A BROAD SPECTRUM, now U.S. Pat. No. 5,786,598, all of which are incorporated herein by reference.

BACKGROUND OF THE INVENTION

The present invention relates to sterilization of target objects by inactivation of microorganisms located thereon and/or therein. More particularly, the present invention relates to parametric control of the pulsed light sterilization of target objects. Still more particularly, described herein are methods and apparatus for parametric control of the sterilization of target objects by deactivation of microorganisms on packages, on or within unpackaged objects and/or on or within the contents of packages, using high-intensity, short-duration pulses of incoherent, polychromatic light in a broad spectrum. Even more particularly, the present invention relates to monitoring and controlling key pulsed light parameters in the deactivation of microorganisms on and/or within target objects using high-intensity, short-duration pulses of incoherent, polychromatic light in a broad spectrum to verify sterilization has been achieved. In a particular embodiment, parametric control of the pulsed light sterilization of the contents of appropriately selected transmissive packaging is described.

Various methods of sterilization are known to those of skill in the art, including for example, heat sterilization, e.g., autoclaving, irradiation sterilization, e.g., using gamma radiation, and chemical sterilization. A more recently developed, and hence less well known, method of deactivating microorganisms on and/or within a target object involves the use of high-intensity, short-duration pulses of incoherent, polychromatic light in a broad spectrum. A significant advantage to this newly developed sterilization and deactivation method is the speed with which it can be accomplished. Most target objects are sterilized or decontaminated within less than a few minutes as only a few flashes, having durations of a few seconds to less than a minute, are required.

Commonly, target objects that are to be sterilized must be further manipulated, after sterilization, to validate the sterilization procedure. For example, if a batch of medical instruments is sterilized using a heat method of sterilization (autoclaving, for example), the so treated instruments may not be used until a random few of them have been tested to confirm that the sterilization method was effective. Typically, the batch of treated products is set aside for a predetermined waiting period following which a few are selected to be tested for the presence of contaminating microorganisms. Assuming the random sampling of batch-treated target objects are demonstrated to be sterile, then the entire batch is released for use. Thus, it can be seen that heretofore known processes of sterilization of target objects are inefficient in that they require further manipulation and testing of the target objects to validate the success of the sterilization, thereby increasing the time necessary to achieve sterilization and increasing the overall costs of such.

Another issue surrounding the need for validation of sterilization processes, is the issue of insuring effective sterilization of target objects contained within packaging. For example, in the case of autoclaving (i.e., heat sterilization), the target object is frequently placed into a package prior to sterilization. Thus, validation is particularly important in order to accommodate the added variable of the packaging material and its affect on the sterilization process. In the case of broad spectrum pulsed light sterilization methods, packaging materials are of particular concern as they must be sufficiently transmissive to the sterilizing light to permit full contact of the light with the target object contained therein.

Polyvinyl Chloride (PVC) is a standard, widely used plastic packaging material used to manufacture flexible containers (bags and pouches) for the administration of small volume parenterals (SVPs), often referred to as mini-bags; large volume parenterals (LVPs); and various enteral nutritional and liquid preparations. These containers are often utilized for patient hydration and/or to supply pharmaceutical preparations, medicines, vitamins, nutritionals, and the like. Heretofore, PVC has proven to be advantageous because of its resistance to heat, which allows the containers to be terminally sterilized using high temperature treatment, i.e., sterilized after filling to deactivate microorganisms inside the containers, including microorganisms suspended in liquid content of the container, using high temperature treatment (e.g., autoclaving).

In many cases, an overwrap is also used to help the flexible containers to survive autoclaving (i.e., high temperature treatment), and also to increase the shelf life of parenteral fluids contained therein by providing improved moisture vapor barrier (MVB) properties, as compared to the MVB properties of PVC alone. In many cases, and particularly for SVP packages (or bags), multiple SVP packages are placed into one overwrap package. Disadvantageously, once the one overwrap package has been opened, the shelf life of the individual SVP packages contained therein is limited to approximately 30 days, because of the poor MVB properties of PVC. Thus, if a practitioner opens an overwrap containing SVPs, but does not use all of the SVPs in a timely manner, the SVP packages must be discarded approximately 30 days after the overwrap is opened. The overwrap also represents a significant added packaging cost and contributes to environmental waste.

Using materials other than PVC, such as olefins (e.g., polyethylene or polypropylene); nylon, or a composite material, having either a laminated or co-extruded structure (including both monolayer and multilayer structures), and the like, for SVP, LVP and/or enteral packages offers a number of significant advantages. One advantage is to reduce or eliminate the use of PVC because of environmental concerns. Another advantage of materials such as polyethylene is that they have much better MVB properties than PVC. For example, in some instances, it may be possible to achieve a longer shelf life (for example, 24 months versus the 15 to 18 months achievable with PVC and overwrap) without the inconvenience and added cost of the overwrap.

Another advantage to replacing PVC with a material such as polyethylene is that products such as pure deionized water (U.S.P. for injection) cannot be effectively packaged in PVC because by-products from the PVC packaging material leach into the pure deionized water, contaminating it, whereas materials such as polyethylene can be formulated so as not to contain by-products that leach into the pure deionized water.

Empty parenteral and enteral containers are also widely used, with liquid contents typically being manually added after delivery of the containers by a pharmacist or dietitian. These empty containers, heretofore typically produced in PVC, are often terminally sterilized using autoclaving. However, these empty containers also suffer from the problems described above. Thus, advantages exist to using olefin, nylon and composite materials for containers, such as parenteral and enteral containers.

Unfortunately, heretofore known methods of terminal sterilization, such as autoclaving, are unsuitable for use with polyethylene containers or thin polypropylene containers, because such containers are unable to withstand the temperatures (e.g., between 100 and 200° C.) or pressures of autoclaving. (Polypropylene containers are able to withstand some amount of commercially useful autoclaving, however, are required to be thicker and more expensive to withstand autoclaving than would need be in the absence of this high heat and pressure treatment.) Thus, there exists a need for an approach to deactivating microorganisms through a container that does not require the use of heat that may damage the container or its contents.

Other processes, such as the process suggested by Beigler, et al. in the U.S. Pat. No. 4,282,863, entitled METHODS OF PREPARING AND USING INTRAVENOUS NUTRIENT COMPOSITIONS, issued Aug. 11, 1981, employ gamma radiation to achieve terminal sterilization. Unfortunately, the use of gamma radiation creates other problems. For example, gamma radiation is prone to altering the polymeric structure of the olefin container (i.e., gamma radiation degrades the product container integrity), which can result in weakened container integrity, leakage, increased gas permeability and other such problems. Also gamma radiation can attack the package and/or its contents to produce other adverse changes, such as darkening, off-colors or color changes, etc. in the package or its contents. Furthermore, gamma radiation inherently causes the generation of highly reactive species, such as hydroxyl radicals produced during the gamma radiation of water, that may detrimentally alter the chemical structure of the product being treated. Thus, there exists a need for an improved sterilization process usable with polyolefins and the like that does not employ gamma radiation, or other such reactive processes, to achieve sterilization.

As mentioned previously, other problems with heat treatment, i.e., autoclaving, and heretofore employed gamma radiation treatment techniques include the "batch" nature of such processes. Specifically, with heat or gamma radiation treatment, products and/or product containers are treated in groups or batches, which problematically requires additional handling of the product not required if an on-line continuous process is used. In addition, careful inventorying and product handling are required in order to assure that each batch is segregated, and separately treated and tested.

In addition, with heretofore employed terminal sterilization techniques, it is nearly impossible to monitor all of the parameters necessary to assure adequate deactivation of microorganisms in all of the product packages in a given batch (i.e., parametric control is nearly impossible). (For example, it is difficult to monitor the temperature within the autoclave at enough points than one can assure that every part of every target object in the batch received enough heat and saturated steam pressure to achieve adequate deactivation of microorganisms.) Because such parametric control is not generally possible with heretofore employed terminal sterilization techniques, the target objects must be observed for a period of time, e.g., for fourteen days, following terminal sterilization to determine whether any contaminants are present in selected (or all) objects from each batch. This, unfortunately, further complicates product and product container treatment and delays usage of the packages and/or products having been treated. An approach that can be performed in a continuous manner, e.g., as a part of a packaging process, can eliminate the need for "batch" handling and "batch" testing. Further, a sterilization approach that allows adequate parametric control over processing parameters to assure adequate sterility levels can eliminate the need for an observation period following treatment and, thus, would be highly advantageous.

It is generally accepted that terminally sterilized articles, such as those used for medical or food applications, must attain greater than a $10^{-6}$ survivor probability among microbial contaminants. In other words, there must be less than once chance in a million that viable microorganisms are present in or on the sterilized article. This level of sterilization is referred to as a sterility assurance level of $10^{-6}$.

Another approach to sterilization of packages, for example, parenteral and enteral containers, involves presterilizing the containers using, for example, autoclaving, gamma radiation, chemical treatments or the like, and then filling such containers in an aseptic environment. A sterility assurance level of $10^{-6}$ is frequently needed for such packages, particularly for containers for parenteral and enteral applications, and is difficult to verify using heretofore known aseptic filling approaches. (Current aseptic processes are validatable at sterility confidence levels of more than approximately $10^{-3}$ by the use of media fills to demonstrate the absence of growth potential.) Thus, the U.S. Food and Drug Administration (USFDA), for example, has stated its preference for terminal sterilization processes, even though it recognizes that many products and product packages are damaged by such processes.

Therefore, what is needed is an approach to deactivating microorganisms at and/or within a target object, which approach achieves an easily verifiable sterility assurance level of at least, for example, $10^{-6}$, but which approach also reduces damage to the target object, including, where present, packaging thereof, such as can occur with current terminal sterilization techniques, such as autoclaving or gamma radiation treatment.

The present invention advantageously addresses the above and other needs.

SUMMARY OF THE INVENTION

The present invention advantageously addresses the needs above as well as other needs by providing methods and apparatus for the deactivation of microorganisms, within and/or on the surface of a target object, using high-intensity, short-duration pulses of polychromatic light in a broad spectrum. More particularly, provided herein are methods and apparatus employing a photo-sensitive detector to monitor and adjust for the deactivation of microorganisms within and/or on the surface of a target object, thereby providing parametric control of the deactivation process such that deactivation of microorganisms is optimized and, most advantageously, providing validation of the sterilization.

Further provided herein is a method of optimizing deactivation of microorganisms on and/or within a target object, using high-intensity, short-duration pulses of polychromatic light in a broad spectrum, by automatically adjusting the intensity and/or duration of light exposure based upon parametric detection of the light. In particular, a photo-sensitive detector is employed to receive a portion of each pulse of light as a measure of the amount of light illuminating the target object and that measurement is used to calculate the degree of deactivation of microorganisms occurring at the surface and/or within the target object. In response to the measurements taken and calculations made, the intensity and/or duration of the pulsed light is adjusted to provide optimized deactivation. Further, these measurements can be, quite advantageously, used to validate sterilization of the target object(s).

In one embodiment, the present invention can be characterized as an apparatus for sterilizing microorganisms at a target object. Such apparatus employs a flashlamp system including means for generating high-intensity, short-duration pulses of polychromatic light in a broad spectrum, and for deactivating microorganisms at and/or within the target object by illuminating the target object with the pulses of light having been generated; a photo-sensitive detector positioned so as to receive a portion of each of the pulses of light as a measure of an amount of light illuminating the target object, for generating an output signal in response thereto; and a control system, coupled to the flashlamp system and the photo-sensitive detector, for determining, in response to the output signal, whether the pulses of light are sufficient to effect a prescribed level of deactivation of microorganisms in and/or on the target object.

In another embodiment, the present invention can be characterized as a method for sterilizing microorganisms on and/or in a target object, having steps of generating a high-intensity, short-duration pulse of polychromatic light in a broad spectrum; deactivating microorganisms at the target object by directing the pulse of light having been generated at the target object; receiving a portion of the pulse of light as a measure of an amount of the pulse of light illuminating the target object; generating an output signal in response to the receiving of the portion of the pulse of light; and determining, in response to the generating of the output signal, whether the pulse of light is sufficient to effect a prescribed level of deactivation of microorganisms in the target object, for example, such that the sterilization process is thereby validated, such as to sterility assurance level of at least about $10^{-6}$.

In a further embodiment, the present invention provides an approach for deactivating microorganisms, and more particularly for deactivating microorganisms within parenteral and/or enteral solutions and packages or containers or contact lens solutions and packages and/or ophthalmic solutions and packages, and within product contents of such packages, using high-intensity, short-duration pulses of incoherent, polychromatic light in a broad spectrum directed at the packages, filled and/or empty, so as to penetrate the packages and deactivate microorganisms on an interior surface thereof and/or suspended within the volume or product contained within the packages.

In a still further embodiment, the invention can be characterized as an apparatus for sterilizing microorganisms in a container. Such apparatus employs the container, which may include, for example, a polyolefin, such as polyethylene, and which transmits light in a spectrum containing wavelengths selected from between about 120 nm and about 2600 nm, e.g., wavelengths between 180 nm and 1500 nm or, e.g., between 180 nm and 300 nm. The container is coupled to a port through which a product within the container can be withdrawn. The port may be, for example, a plastic tube or cap having a puncture site at which it is designed to be punctured for administration of its contents, or may be a cap that is unscrewed or otherwise removed before administration. Such ports are well known in the art. A flashlamp system generates high-intensity, short-duration pulses of polychromatic light in a broad spectrum, and the pulses of light generated by the flashlamp illuminate the container and deactivate microorganisms within the container.

In a variation of this further embodiment, an interface region at which the port is bonded to the container is also illuminated and microorganisms within the port and at the interface region are deactivated by the high-intensity, short-duration pulses of incoherent, polychromatic light in a broad spectrum.

In another embodiment, the invention may be characterized as an apparatus for deactivating microorganisms in a container that employs the container, which, in this embodiment, contains a transmissive product that transmits more than about one percent of light at a wavelength of about 260 nm, and which container transmits light in a spectrum having wavelengths selected from between 120 nm and 2600 nm (see examples above). The embodiment also employs a port coupled to the container through which the product within the container can be withdrawn, and a flashlamp system that generates high-intensity, short-duration pulses of polychromatic light in a broad spectrum, and deactivates microorganisms within the container by illuminating the container with such pulses of light.

In a further embodiment, the invention can be characterized as an apparatus for deactivating microorganisms in a container. The apparatus of this embodiment employs the container, which in this embodiment transmits light in a spectrum including wavelengths selected from between about 120 nm and about 2600 nm (see examples above); and a port coupled to the container through which a product within the container can be withdrawn; and a flashlamp system that generates high-intensity, short-duration pulses of polychromatic light in a broad spectrum, and deactivates microorganisms within the container and port by illuminating the container and port with the pulses of light.

In an additional embodiment, the invention can be characterized as an apparatus for deactivating microorganisms in a container employing the container, which includes at least one port through which the product within the container can be withdrawn, and transmits light in a spectrum having wavelengths selected from between about 120 nm and about 2600 nm (see examples above); a flashlamp system that generates high-intensity, short-duration pulses of polychromatic light in a broad spectrum, and deactivates microorganisms within the container by illuminating the container with the pulses of light having been generated. The flashlamp of this embodiment advantageously deactivates sufficient microorganisms to achieve a sterility assurance level of at least $10^{-6}$.

In yet another embodiment, the invention can be characterized as an apparatus for sterilizing microorganisms in a container. The container of such embodiment includes a blister formed therein, and a backing material that together with the blister forms a cavity in which is contained a contact lens and a preservative fluid. The preservative fluid is at least one percent transmissive to light having a wavelength of about 260 nm. A flashlamp system generates high-intensity, short-duration pulses of polychromatic light in a broad spectrum that deactivate microorganisms within the container by illuminating the container with the pulses of light having been generated.

BRIEF DESCRIPTION OF THE DRAWINGS

The above and other aspects, features and advantages of the present invention will be more apparent from the following more particular description thereof, presented in conjunction with the following drawings wherein:

FIG. 3 is a schematic diagram of an apparatus for fabricating, filing, sealing and sterilizing a parenteral or enteral package;

FIG. 4 is a side view diagram of an exemplary parenteral package suitable for use in a sterilizing chamber (or tunnel) of the apparatus of FIG. 2;

FIG. 5 is a perspective view of another exemplary parenteral package suitable for use in a sterilizing chamber (or tunnel) of the apparatus of FIG. 3;

Corresponding reference characters indicate corresponding components throughout the several views of the drawings.

DETAILED DESCRIPTION OF THE PREFERRED EMBODIMENTS

The following description of the presently contemplated best mode of practicing the invention is not to be taken in a limiting sense, but is made merely for the purpose of describing the general principles of the invention. The scope of the invention should be determined with reference to the claims.

In order to provide effective sterilization of a target object with pulsed light, it is important not only that the pulsed light reach all the important surfaces and/or volumes of the target object, but also that such pulsed light be of sufficient strength and duration to accomplish the desired level of deactivation and/or sterilization. Optimization of the pulsed light requires consideration of the spectral content of each flash of light, the energy of each flash (or fluence-per-flash in Joules/cm$^2$/flash) and the number of flashes delivered. Advantageously, the present invention provides apparatus and methods wherein these three parameters are reliably measured during pulsed light treatment and the measurements thereof are used to control the sterilization process. In accordance with preferred embodiments herein, these three parameters and/or other relevant parameters are monitored, controlled, and verified during pulsed light treatment operations, thereby allowing for validation of the treatment, i.e., verification that sufficient sterilization is achieved. This validation of the sterilization treatment can, advantageously, be based on measurements of the described parameters alone, as opposed to being based upon observation of the treated products or packages for signs of microbial activity following a waiting period.

Figure 1:
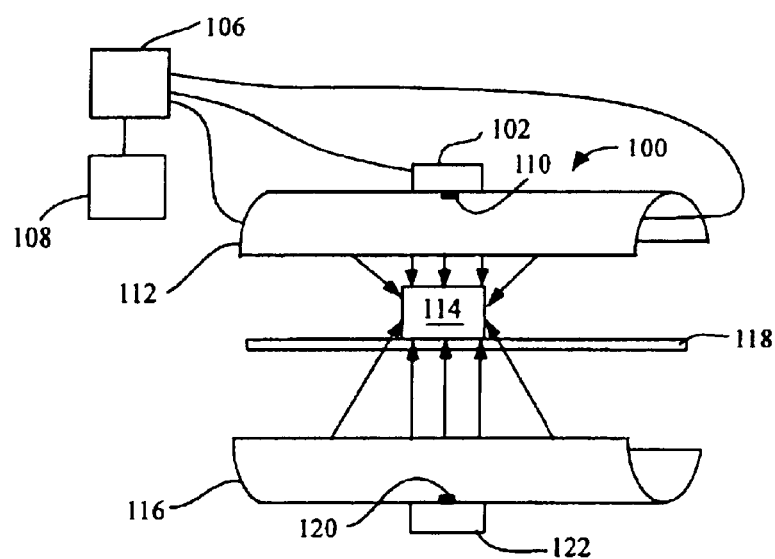
FIG. 1 is a schematic diagram of an apparatus for sterilizing a target object wherein the sterilization is parametrically controlled.

Referring first then to FIG. 1, illustrated is an apparatus for sterilizing a target object in accordance herewith, wherein the sterilization is parametrically controlled. The target object 114 is located within the sterilization chamber, sitting on top of shelf 118 which is formed of material selected to be at least about 10% transmissive, preferably at least about 50% and more preferably at least about 90% transmissive to light in a spectrum containing wavelengths selected from between about 120 nm to about 2600 nm, e.g., wavelengths between about 180 nm to about 1500 nm, e.g., between about 180 nm and about 300 nm. Examples of suitable material for the shelf include, without limitation, quartz and sapphire.

Surrounding the target object 114 and shelf 118 are flashlamps (not illustrated), which flashlamps are preferably surrounded by reflector systems 112, 116. The reflector system is used to focus or concentrate the light onto the target object 114 to be treated. In the illustrated embodiment, a photodetector 102 is positioned on the reflector system over a pinhole 110, through which pinhole light from a flashlamp passes. As discussed in greater detail with respect to FIG. 2, the monitor and control circuitry 106 receives data from the photodetector 102 and monitors preselected operating parameters from the flashlamp. Based upon this information, the monitor and control circuitry 106 controls the operation of the flashlamp. Suitable monitor and control circuitry are well known in the art, including for example as illustrated in FIG. 1, data acquisition and control cars added to a personal computer 108 may be used.

In the preferred embodiment illustrated in FIG. 1, there are pinholes 110, 120 and photodetectors 102, 122 employed on the reflector system over each flashlamp. In this way the operation of each individual flashlamp may be separately monitored and controlled to optimize sterilization of the entire surface and/or volume of the target object 114. It will be appreciated by those of skill in the art that the photodetectors or other detection apparatus may alternatively be placed elsewhere within the sterilization chamber, but is preferably placed such that no portion of the detection apparatus interferes with or blocks any portion of the path of the treatment light towards the object. It will be further appreciated, by those of skill in the art, that the entirety of the sterilization chamber is not illustrated in FIG. 1, for example, the exterior shell, doors and/or other means for inserting and removing the target object from the sterilization chamber are not shown. However, such apparatus is well known, examples of which are readily available, for example, from PurePulse Technologies, Inc. of San Diego, Calif. as PUREBRIGHT Model No. PBS-1 as well as previously described, for example, in U.S. Pat. No. 5,900,211, issued on May 4, 1999 to Dunn, et al., which patent is hereby incorporated by reference in its entirety.

Significantly, the heretofore known methods and apparatus for detecting radiation, in particular ultraviolet radiation, used for decontamination, have been used in systems designed for decontaminating fluids, such as water. See for example, PCT Patent Application No. WO 82/01703, issued to International Farvefabrik on May 27, 1982, describing a photocell positioned in contact with or nearly in contact with a fluid being treated and opposite the radiation source, in this case an ultraviolet lamp. Apparently, what is detected in the system described in the WO 82/01703 application is the UV radiation permeating the water being treated. In contrast, the present method and apparatus are designed for use with solid target objects contained within a pulsed light sterilization chamber. In such a system, it is not advisable to place a photocell or other detection apparatus in close proximity to the target object as such would necessarily block the path of some of the pulsed light, thereby resulting in a portion of the target object being incompletely treated. Further, a detection system in accordance with the present invention must take into consideration the fact that the light being detected is not that passing through the target object but rather is the light being delivered to the object.

Importantly, the apparatus of the WO 82/01703 application is designed to simply monitor the ultraviolet radiation, not to control or validate the sterilization process. Only when the detected radiation falls below a predetermined level does any change to the process occur and that control is limited to stopping the flow of liquid through the disinfection apparatus and sounding an alarm. This is in contrast to the parametric control of the present invention. Not only is the presently described invention useful for warning of a failure in the sterilization process, but it is useful for providing repeated and/or continuous control of the sterilization process by detecting predetermined characteristics of the pulsed light and then adjusting the pulsed light treatment to be within prescribed parameters, thereby insuring sterilization of the target object and permitting validation of the process.

Figure 2:
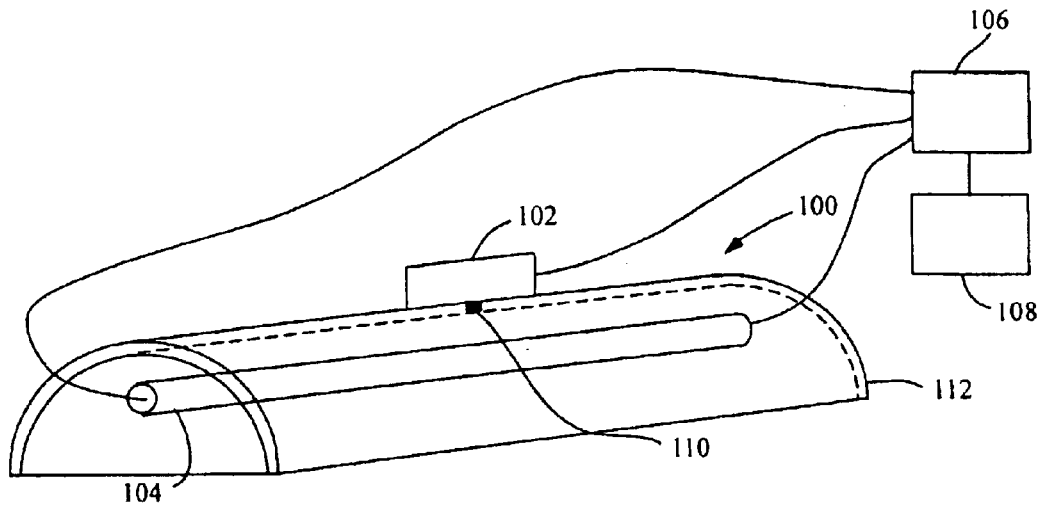
FIG. 2 is a perspective view of a portion of the sterilization chamber of FIG. 1, illustrating the photodetector used to measure the character of the treatment light from a flashlamp, such as by measuring fluence per flash, in order to maintain parametric control over sterilization of packages and their contents in such sterilization chamber.

Referring now to FIG. 2, which illustrates a perspective view of a section of the apparatus of FIG. 1, a more detailed explanation of the parametric control of the sterilization process is provided. A photodetector 102 is used to measure fluence-per-flash of light emitted from a corresponding flashlamp 104. This information is then communicated from the photodetector 102 to suitable monitor and control circuitry 106. The monitor and control circuitry then monitors and controls the fluence-per-flash of the light, i.e., the energy-per-flash, within a prescribed spectral bandwidth; the total energy over some preselected treatment time; the spectral energy within a preselected bandwidth over time; and/or any of a range of other detectable parameters based upon the measurement of fluence-per-flash. In a similar fashion the pulse parameters involved in energizing the flashlamp 104, such as current, peak current, current waveshape, voltage, voltage waveshape, and/or any of a range of other pulse parameters may be monitored and controlled by the monitor and control circuitry 106, such as is known in the art. The output from the monitor and control circuitry 106, monitoring both the flashlamp energizing parameters and the resulting flash parameters, completely describe the operation of pulsed light generation within the treatment chamber 100. As stated above, suitable monitor and control circuitry 106 is readily available, such as data acquisition and control cars that can be added to a personal computer 108.

Electronic output of the monitor and control circuitry 106, in combination with appropriate programmatic control by the personal computer 108, can be used to monitor, adjust, and document pulsed light treatment. By providing instantaneous electronic signals indicative of parameters related to system operation, in the presence of operation or output outside of a preselected range, feedback circuits in the monitor and control circuitry 106 and programmatically embodied in the personal computer 108 can easily be arranged to adjust system operating parameters and output in accordance with well known feedback/control system approaches.

For example, ultraviolet output from the flashlamp 104 can be coupled to lamp voltage and current operating circuitry in the monitor and control circuit 106 through appropriate feedback/control system circuitry. By monitoring ultraviolet output, system performance can be monitored, adjusted, and maintained each in preselected minima and maxima by coupling this information to circuit pulses through appropriate feedback control system circuitry. Similarly, fault detection circuitry within the monitor and control circuitry 106 can be used to summon an operator, shut down the system, or otherwise perform system oversight and alert operations should pulse or output parameters fall below or outside desired levels. In addition, quality control documentation can be performed on-line and in an instantaneous fashion by feeding the electronic signals from operation monitoring systems and output monitoring systems into the personal computer 108 or other computer or electronic storage device.

For pulsed light treatment, a wide range of photodetectors and photooptics may be adapted in a variety of ways to monitor, control, and verify that a proper pulsed light sterilization treatment has been achieved. For example, a variety of photooptical methods and detectors are available that can be used to "look at" or interrogate each treatment flash to confirm that the light pulse produced was of the desired intensity, and contained the proper spectral distribution and content. Components for appropriate monitor and control systems are available from a variety of sources and one skilled in the art of photodetector or photooptical systems can design and assemble appropriate systems. For example, surface or volume absorbing calorimeter systems that can be used to monitor the pulsed light fluence per flash or total light output are available from many sources (Gentec, Ophir, Molectron, Digirad, etc.). Similarly, photodetector systems that alone or in combination with appropriate filters or other components are widely available (Hamamatsu, Phillips, EG&G, UDT Sensors, etc.) and can be used to examine the UV content or spectral distribution of the pulsed light flash. The pulsed light can be collected and monitored using a wide variety of means. For example, fiber optic probes, focusing or defocusing lenses, integrating spheres, CCD arrays, etc. can be used to collect light from wide or narrow angles or provide spatial resolution of multipoint analysis for the light imaging system. Components or systems for light collecting, handling, monitoring and analyzing are available from many sources; and these components or systems can be designed and assembled by and from a large number of manufacturers or suppliers.

An important consideration, of course, in designing and implementing parametric control and validation of the broad spectrum, pulsed light sterilization process in accordance herewith, is that the means chosen for detecting the light within the chamber, such as a photodetector or photooptical system, be positioned within the chamber such that no obstruction exists between it and the flashlamp. Additionally, the light detecting means should not be placed within the chamber in such a way that it obstructs the path of any light intended to contact the target object. Thus, for example, where traditional means of measuring the sterilization environment will permit location of the detection apparatus on the target object, such is not appropriate where light is the sterilizing medium as the detection apparatus would shield a portion of the target object from the sterilizing light.

In a heat sterilization chamber, for example, a thermometer (or other temperature detection means) is preferably placed near, on or even within the object being sterilized in order to insure the object is completely exposed to the desired temperature. In contrast, the broad spectrum light used in the present invention will be obstructed by detection means placed proximate to the target object. Hence, the preferred placement of the light sensitive device (e.g., photodetector or photooptical system) is proximal the light source (i.e., the flashlamp). However, as previously described, the flashlamp is preferably partially surrounded by a reflector (see 112 in FIGS. 1 and 2). Thus, to insure that the flashlamp/reflector system is operating optimally, it is further preferable that the light sensitive device not interfere with the path of the light towards the reflector, for example that the detector be recessed within or flush with the reflector.

A preferred method of quantifying the light signature of a pulsed light treatment flash is shown in FIG. 2. A sample of the light flash is collected via a small diameter hole 110, or "pinhole" 110, located in a reflector 112 system used to focus or concentrate the light onto the target object to be treated. The pinhole 110 in the reflector 112 transmits light to one or more light sensitive devices (photodetectors 102), such as photometer, a photomultiplier, a calorimeter, a pyroelectric joulemeter, a bolometer, a diode or diode array, or other photosensitive or photodetector system. The photodetector 102 can be used to sample the character (e.g., fluence-per-flash and spectral content) of the treatment light through a variety of means. The light can be "viewed" directly or passed through a sampling port, lens, or likewise apertured, collimated, filtered, focused, defocused, reflected, refracted, or otherwise handled, manipulated, or collected before evaluation.

One, or more photodetectors can interrogate the treatment light from one or more flash lamps with or without an appropriate filter or filters so that fluence-per-flash and/or spectral distribution can be monitored and controlled.

The signal from the photodetector 102 varies temporally with the fluence-per-flash, and with an appropriate filter or filters such can be specific to a particular portion of the light spectrum. For example, since the ultraviolet fluence-per-flash is generally of importance, the photodetector 102 can measure the fluence-per-flash of only the ultraviolet portion of the spectrum through the use of an appropriate ultraviolet bandpass filter. The output of the photodetector 102 can be integrated so as to measure the total ultraviolet energy of the light pulse in the selected bandwidth. This integrated signal is then recorded by either a computer or other means to provide a permanent record of the total energy of the light pulse, and, over time, the entire pulsed light treatment process.

Another key factor is calibration of the measuring system. Many approaches are contemplated for calibration. In accordance with one approach, an ultraviolet calorimeter is placed in the treatment chamber in place of the target object. The calorimeter measures the ultraviolet energy of the light pulse, and is traceable back to international standards. Measurements taken by the calorimeter can thus be compared to measurements taken by the photodetector, so as to calibrate the photodetector to international standards. In a second approach, the light passing through or reflected from the target object is measured by the calorimeter. A third approach, of course, is to simply calibrate the photodetection apparatus outside of the sterilization chamber then reinstall the detector. Other calibration methods are known to those of skill in the art and are likewise contemplated herein.

In general, for treatment with pulses of light, the target object is preferably moved through or located in the treatment area in such a manner that the complete object surface and/or complete object is treated. Where the target object is to be sterilized and subsequently packaged, it is preferably maintained in a sterile environment until fully packaged. For example, a medical instrument may be the target object in a sterilization process in accordance herewith. The untreated medical instrument is conveyed into the treatment area of the sterilization chamber where it is treated with pulsed light. Following treatment, while still located in the sterilization chamber, the medical instrument is then conveyed, for example by a conveyor belt, by rollers or by other mechanical means, to a packaging area. In the packaging area, the treated medical device is sterilely packaged, using methods and apparatus known to those of skill in the art. For example, the target object, such as a medical instrument, may be placed in a sterile polymer package, which package is then sealed, such as by heat sealing, to maintain sterility therein.

Another example contemplated herein, is the use of the parametrically controlled pulsed light sterilization apparatus to sterilize food products prior to and/or in conjunction with packaging thereof. For example, a solid food product, such as a bagel or other bread product, sausage or other meat product and/or egg is passed through the treatment area of the sterilization chamber and then packaged using well known methods. While the materials typically employed to package such food products are not airtight nor, typically, sterile, the packaging process is typically aseptic or at least very clean. Further, it will be readily appreciated that a sterilized food product would be expected to have a longer shelf life than a non-sterilized food product, regardless of the packaging of the product. Thus, for example, before eggs are placed into a carton, their exterior surface may be quickly decontaminated and/or sterilized using the presently disclosed methods and apparatus, thereby reducing the risk of contamination from, for example, salmonella and/or other superficial microorganisms. Similarly, bread products and/or meat as they are conveyed, for example, from a processing point to a packaging point may, advantageously, be decontaminated and/or sterilized using the parametrically controlled method and apparatus of the present invention and thereafter packaged. By parametrically controlling this process of food decontamination/sterilization, the cleanliness of the packaging process can be validated, for example, in accordance with government regulation.

Alternatively to packaging the target object after sterilization (or decontamination) thereof in accordance with the present invention, the object may be removed from the sterilization chamber and immediately used. For example, it is envisioned that a parametrically controlled pulsed light sterilization chamber in accordance herewith may be located in an operating room. Should an instrument or other sterile object come in contact with a non-sterile surface or environment (such as when a medical instrument falls to the floor of the operating room), that object may be placed into the sterilization chamber, subjected to an appropriate number of parametrically controlled pulsed light flashes and thereby re-sterilized. Advantageously, most such target objects will be sterilized by exposure to only a few flashes of light having durations of a few seconds or less, thereby allowing the surgeon to quickly return to the surgery. While medical instruments are described herein, it will be appreciated by those of skill in the art that numerous and varied other objects may be sterilized using the parametrically controlled sterilization methods and apparatus of the present invention. For example, food products, toys, utensils, gloves, combs and other objects may be used in the present system. It will be appreciated, of course, that only those portions of the target object that are fully contacted by the pulsed light will be sterilized thereby. In addition to sterilsation of unpackaged items, it may be desirable to sterilize the exterior surface of a package or container and such is likewise therefore contemplated herein. Thus, appropriate location of the target object within the sterilization treatment zone is important.

In yet another alternative, target objects may be prepackaged in a packaging material that is sufficiently transmissive to the pulsed light to permit sterilization of the product within the package. Where transparent packages are used, the process of sterilization and, hence, of parametric control thereof becomes more complex due to internal reflection and refraction of the light as it passes into the package. The following are examples of package transport approaches.

Turning to FIG. 3, a diagram of an apparatus 10 for fabricating, filling, sealing, and sterilizing a parenteral or enteral package 12 is shown. A roll 14 (or other supply) of packing material is fed by, for example, rollers 15, into a fabricating, filling and sealing apparatus 16, such as are known in the art. Alternatively, the packaging material may assume a form of resin beads, as would be the case typically in a blow/ fill/seal apparatus. The fabricating, filling and sealing apparatus 16 may be a form/fill/seal apparatus; a blow/fill/seal apparatus; an injection blow molding apparatus; an extrusion and coextrusion blow molding apparatus; a film/sheet extrusion and coextrusion apparatus; a thermoforming apparatus; or an injection molding apparatus, such as are known in the art. Various sealing equipment and techniques may be employed including heat sealing, radio frequency (RF) fabrication, hot plate welding, induction welding, and/or spin welding, all of which are well known in the art.

Also shown, is a treatment zone, or sterilization tunnel, 18 (sterilizing chamber 18) through which fabricated, filled and sealed parenteral or enteral packages are passed, by, for example, a conveyer belt 20, in order to sterilize such packages. The conveyer belt 20 may employ one or more quartz shelves on which the parenteral or enteral packages rest while they are conveyed, or one or more hooks from which the parenteral or enteral packages hang while they are conveyed or any of a number of other well known means of conveyance. In this way, the parenteral or enteral packages are not shielded from light as they pass through the sterilizing chamber 18.

The forming, filling and sealing apparatus 16 may, as mentioned above, be of a type well-known in the art, and preferably is capable of manufacturing containers (or packages) at high speeds, and with from one to multiple cavitations.

One example of a suitable blow/fill/seal apparatus adaptable for use with the present embodiment is marketed under Model No. 603 by Automatic Liquid Packaging, Inc. of Illinois. Another such apparatus is marketed under Model No. 624 by Automatic Liquid Packaging of Woodstock, Ill.

A suitable form/fill/seal apparatus utilizes an extruded film to form a pouch or bag. One example of such a form/fill/seal apparatus adaptable for use with the present embodiment is marketed as System Model Mark III by Inpaco of Allentown, Pa.

Both the blow/fill/seal apparatuses and the form/fill/seal apparatuses mentioned above permit the attachment of fitments (see FIGS. 4 and 5) during formation of the package or container.

The sterilizing chamber 18, as shown, may consist of one or more reflectors 22, and one or more flashlamps (not shown), such as are available as Part No. 01812-525 from PurePulse Technologies, Inc., of San Diego, Calif. Such flashlamps and attendant pulse-generating hardware (not shown) are capable of generating high-intensity, short-duration pulses of incoherent polychromatic light in broad spectrum. Suitable flashlamps and attendant pulse generating hardware are described in U.S. Pat. No. 4,871,559 (METHODS FOR PRESERVATION OF FOODSTUFFS); U.S. Pat. No. 4,910,942 (METHODS FOR ASEPTIC PACKAGING OF MEDICAL DEVICES); and U.S. Pat. No. 5,034,235 (METHODS FOR PRESERVATION OF FOODSTUFFS), issued to Dunn, et al. (the '559, '942 and '235 patents, respectively), incorporated herein by reference as if set forth in their entirety. As will be appreciated by the skilled artisan, numerous known and yet-to-be-developed variations of the flashlamps and pulse generating hardware are suitable for use in the embodiments disclosed herein.

The one or more reflectors 22 direct light from the flashlamps toward completed parenteral or enteral packages 12. Preferably, the reflectors 22 are made from, for example, aluminum, and optimally reflect light across the entire spectrum of light generated by the flashlamps. Advantageously, the reflectors may be designed, using commonly known design techniques, to create a uniform or non-uniform energy distribution of light across the parenteral or enteral package being illuminated. In this way, for example, greater amounts (i.e., concentrations) of light energy can be directed, for example, at thicker portions of the parenteral or enteral package, such as around an additive port and/or an administration port; and/or at portions of the product contained therein, such as near the middle of the parenteral or enteral package where a greater volume of product needing treatment may be present.

In accordance with the present embodiment, the pulses of light pass through the parenteral or enteral packages 12, reaching the contents of such packages, and effecting sterilization or deactivation of microorganisms at the interior of the packages 12 and suspended within products contained in the packages 12.

In this way, an effective method is provided for sterilizing, not only parenteral or enteral packages, but product contents thereof, without requiring the high temperature processes involved in autoclaving. In addition, other product containers and products contained therein may be treated using the approach of this embodiment. For example, contact lens packages and the contact lenses contained therein can be treated using the above-approach. As a result, materials such as Olefins, nylon, and composite materials may advantageously be employed in product packages, instead of more conventional materials, such as polyvinyl chloride (PVC). Because Olefins, nylon, and composite materials can have superior moisture vapor barrier characteristics to those of PVC, and may not contain components that are readily absorbed into the products contained therein, the above apparatus and attendant methods, provide a vastly superior forming, filling, sealing and sterilizing approach than has heretofore been available. Furthermore, the present embodiment achieves a sterility assurance level of at least $10^{-6}$, and does not require the use of gamma radiation or other highly degradative processes.

Referring to FIG. 4, a typical small volume parenteral container 12 or large volume parenteral container 12 configuration is shown (generically referred to herein as a bag assembly 12). The bag assembly 12 employs a flexible pouch 30, made in the preferred embodiment from a polyolefin, such as polyethylene, to which a fitment 32 is joined. The fitment 32 generally includes two short tubes 36, 38 (or ports), through which a connection can be made for delivery of a liquid from the flexible pouch 30 (or parenteral pouch) to a feed tube (not shown), or to the flexible pouch, such as by a practitioner (often a pharmacist or nurse) when making an additive to the flexible pouch 30.

One port 36, the port used to make an additive, is typically referred to as an additive port 36, and another port 38, the port used for delivery of fluid, is typically referred to as an administration port 38. With a device referred to as an intravenous set (not shown), which is "spiked", i.e., punctured through, at the administration port 36, the flexible pouch's 30 contents can be delivered to a patient, either by gravity or with the use of a pump or controller (not shown).

Enteral containers (not shown), made preferably from polyolefins, such as polyethylene, utilize similar fitments, however, an enteral set (or spike set) and flexible tubing used with the enteral container is typically used to deliver liquid to a patient's stomach by a variety of methods, such as through a gastronomy tube for, for example, liquid feeding.

The flexible pouch 30 is preferably constructed of materials that transmit light in a spectrum of from, for example, between 180 nm and 1500 nm. Many materials, such as Polyethylene, Polypropylene, EVOH, nylon and a number of other plastic materials, either monolayer or multilayer, readily transmit this spectrum and can be used, in accordance with variations of the present embodiment.

The joining of the fitment 32 to the flexible pouch 30, and the filling of the flexible pouch 30, can preferably be conducted in an aseptic environment, such as a HEPA-filtered chamber, in a packaging machine, to minimize introduction of contaminants, such as microorganisms. (Such HEPA-filtered chambers are well known in the art.) The fitment 32 can be joined to the flexible pouch 30 by heat sealing, radio frequency (RF) welding or "plastic welding" techniques of the type commonly known in the art. An alternative example of a parenteral package suitable for use with the embodiment of FIG. 3 is shown in FIG. 5.

Figure 6:
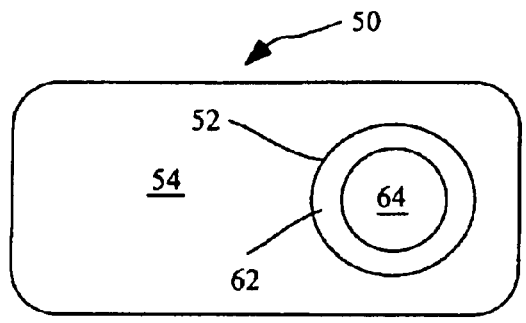
FIG. 6 is a top view of a contact lens package, having a "hemispherical" blister, and being suitable for use in the sterilizing chamber (or tunnel) of the apparatus of FIG. 3.

Referring to FIG. 6, a top view is shown of a contact lens package 50, having a "hemispherical" blister 52, and being suitable for use in the sterilizing chamber (or tunnel). The contact lens package 50 has a polyolefin panel 54 (such as a polyethylene or polypropylene panel) into which is formed the blister 52. The blister 52 protrudes from a top side 56 (FIG. 7) of the polyolefin panel 56, and a lid stock which may include foil backing 58 (FIG. 7) is adhered to the a bottom 60 of the polyolefin panel 54. Between the lid stock 58, and an interior of the blister 52 is formed a cavity 62 that is filled with a preservative fluid, such as saline solution, and a contact lens 67, such as a soft contact lens.

High-intensity, short-duration pulses of incoherent polychromatic light 66 (FIG. 7) are in practice directed at the top 56 of the polyolefin panel 54, and at the sides of the blister. The high-intensity, short-duration pulses of incoherent polychromatic light 66 (FIG. 7) have an intensity, duration, and wavelength or wavelengths as follows: intensity of from 0.01 J/cm² to 50 J/cm², e.g., 0.05 J/cm² to 5 J/cm², e.g., 2 J/cm²; duration of from 0.001 ms to 100 ms, e.g., 0.3 ms; and wavelengths selected from between 120 nm and 2600 nm, e.g., wavelengths between 180 nm and 1500 nm or, e.g., between 180 nm and 300 nm. The high-intensity, short-duration pulses of incoherent polychromatic light 66 (FIG. 7) penetrate the blister 52, which is substantially transparent to light having wavelengths in the range selected, and impinge upon the preservative fluid and contact lens 64 contained therein. As a result, microorganisms at the interior of the blister 52, suspended in the preservative solution, and on or in the contact lens 64 are deactivated.

Advantageously, the contact lens 64 is sealed within the polyolefin package 50 prior to illumination of the package 50 with the high-intensity, short-duration pulses of incoherent polychromatic light, therefore preventing contamination of the interior of the blister, the preservative fluid, or the contact lens 64 following treatment (i.e., illumination). Also advantageously, the high-intensity, short-duration pulses of incoherent polychromatic light do not degrade the polyolefin panel 54, the lid stock 58, or the contact lens 64 contained thereinbetween.

Thus, a terminal sterilization approach is provided for use with a sealed contact lens package that, unlike heretofore known autoclaving and gamma radiation treatment approaches, does not result in degradation of the package being treated or the contact lens contained therein.

Figure 7:
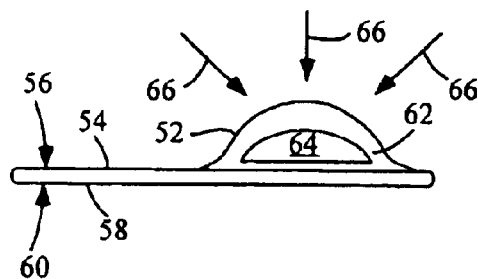
FIG. 7 is a side view of the contact lens package of FIG. 6, being suitable for use in the sterilizing chamber (or tunnel) of the apparatus of FIG. 3.

Referring then to FIG. 7, a side view is shown of the contact lens package 50 of FIG. 6, being suitable for use in the sterilizing chamber (or tunnel) of the apparatus of FIG. 3. Shown are features of the contact lens package 50 of FIG. 6, with the top and the bottom of the package being more clearly identified, and with arrows representing the high-intensity, short-duration pulses of incoherent polychromatic light 66 as they are directed at the blister 52. Similar features bear similar reference numerals to those in FIG. 6.

Figure 8:
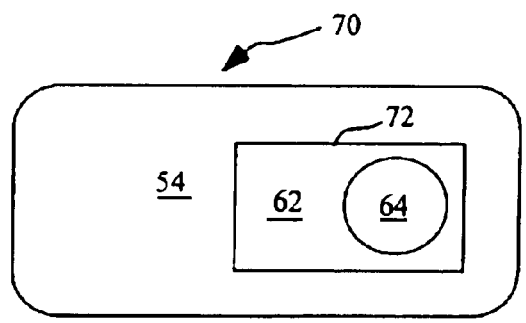
FIG. 8 is a top view of a contact lens package, having a "rectangular" blister, and being suitable for use in the sterilizing chamber (or tunnel) of the apparatus of FIG. 3.

Referring to FIG. 8, a top view is shown of a contact lens package 70, having a "rectangular" blister 72, and being suitable for use in the sterilizing chamber (or tunnel) of the apparatus of FIG. 3. The contact lens package 70 of FIG. 8 is substantially similar to the contact package 50 of FIG. 8, except that the blister 72 is generally rectangular in shape. The sterilization approach described above in reference to FIG. 6, however, can be employed with similar effectiveness to the contact lens package of FIG. 8. Features shown in FIG. 8 that are similar to features of FIG. 6 bear similar reference numerals.

Figure 9:
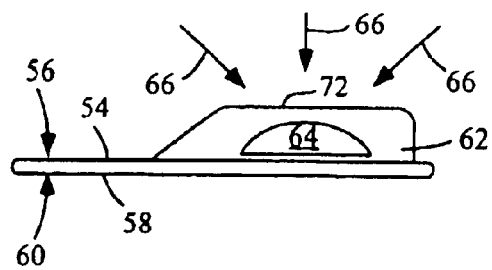
FIG. 9 is a side view of the contact lens package of FIG. 8, being suitable for use in the sterilizing chamber (or tunnel) of the apparatus of FIG. 3.

Referring to FIG. 9, a side view is shown of the contact lens package 70 of FIG. 8, being suitable for use in the sterilizing chamber (or tunnel) of the apparatus of FIG. 3. Shown are features of the contact lens package of FIG. 8, with the top 56 and the bottom 60 of the package 70 being more clearly identified, and with arrows representing the high-intensity, short-duration pulses of incoherent polychromatic light 66 as they are directed at the blister. Similar features bear similar reference numerals to those in FIGS. 6 and 8.

Figure 10:
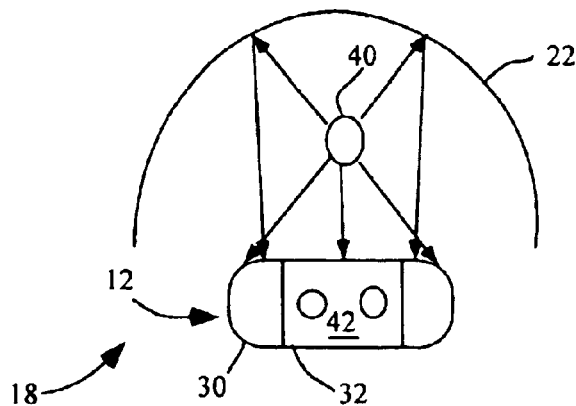
FIG. 10 is an end view of the parenteral package of FIG. 4 and one variation of a sterilizing chamber of the apparatus of FIG. 3.

Referring next to FIG. 10, and end view is shown of the sterilizing chamber 18 of FIG. 3. In the variation shown, a single reflector 22 is positioned around a flashlamp 40 and above a parenteral container 12 as it is passed through the sterilizing chamber on, for example, a conveyor belt (not shown). The parenteral container 12 could easily be replaced by an enteral container or a contact lens container as applications demand.

In accordance with the present embodiment, high-intensity, short-duration pulses of polychromatic light in a broad spectrum are directed at the flexible pouch 30 and fitment 32 as they pass through the sterilizing chamber 18. Typically, the intensity of the pulses is from 0.01 J/cm$^2$ to 50 J/cm$^2$, e.g., 0.05 J/cm$^2$ to 5 J/cm$^2$, e.g., 2 J/cm$^2$. Advantageously, a high degree of deactivation of microorganisms within the flexible pouch 30, including deactivation of microorganisms suspended within fluid contained in the flexible pouch 30, deactivation of microorganisms at an interface 42 between the fitment 32 and the flexible pouch 30, and deactivation of microorganisms on or within the fitment 32, are effected by the pulses of light.

In some cases, the fitment 32 may not be sufficiently transmissive to permit complete sterilization of the fitment 32 with the high-intensity, short-duration pulses of polychromatic light in a broad spectrum. However, if a sufficiently transmissive material is selected for the fitment 32, and if an appropriate shape and thickness for the fitment is selected, such fitment 32 can be sufficiently sterilized with high-intensity, short-duration pulses of polychromatic light in a broad spectrum. Selection of a fitment design suitable for sterilization using high-intensity, short-duration pulses of polychromatic light in a broad spectrum is well within the abilities of the skilled artisan.

In accordance with the present embodiment and in the event the fitment cannot be completely sterilized using high-intensity, short-duration pulses of polychromatic light in a broad spectrum, an internal portion of the fitment 32 may be pre-sterilized with heat or gamma-radiation, before being joined to the flexible pouch. An interface region 42, such as shown best in FIG. 5, at the periphery of the fitment 32, whereat the fitment 32 is joined to the flexible pouch 30, can be treated with the high-intensity, short-duration pulses of polychromatic light in a broad spectrum before and/or after the flexible pouch 30 is filled with fluid, thereby deactivating microorganisms at, in or near the interface region. Such pulses of light preferably have an intensity in the ranges mentioned above, i.e., 0.01 J/cm$^2$ to 50 J/cm$^2$, e.g., 0.05 J/cm$^2$ to 5 J/cm$^2$, or 2 J/cm$^2$ (measured at the interface of the fitment 32 with the flexible pouch 30).

The above-described pulsed light process uses high-intensity, short-duration pulses of polychromatic light in a broad spectrum, i.e., "white" light, to deactivate a wide range of microorganisms, including microbial and fungal spores. During each flash, the intensity of the light is about 90,000 times the intensity of sunlight at the earth's surface, i.e., the "high-intensity" of the light is from between 0.01 J/cm$^2$ to 50 J/cm$^2$, e.g., 0.05 J/cm$^2$ to 5 J/cm$^2$ or 2 J/cm$^2$, measured at the microorganisms to be deactivated. Each pulse, or flash, of light has a duration of only a fraction of a second (e.g., a "short duration" of from between 0.001 ms to 100 ms, e.g., 0.3 ms).

The flashes are typically applied at a rate of about 1–20 flashes per second and, for most applications, a few, i.e., 1 through 3, flashes applied in a fraction of a second provide a very high level of microorganism deactivation, or kill. The duration of the light pulses is typically from between 200 and 300 μs.

The process of the present embodiment uses a technique referred to herein as pulsed energy processing. By storing electrical energy in a high energy density electrical storage capacitor, and releasing it in high-energy, short-duration pulses, high peak power levels are achieved. Such high-peak, power levels of electrical energy can be used to create the high-intensity, short-duration pulses of polychromatic light in a broad spectrum. (Pulsed energy processing is described in the '559, '942 and '235 patents, previously incorporated herein by reference.) The high intensity of these pulses of light results in a unique bactericidal effect not observed when the same energy is provided at low intensity in sustained or continuous wavelength (CW) applications. Although the peak power of each pulse is preferably very high, because of its short duration, the total energy in each pulse is relatively low, and the average power requirement ("wall plug power") is modest. Thus, the process is not only effective, but is economical with respect to energy consumption.

The pulses of light are generated by electrically ionizing a xenon gas lamp, causing it to emit broad band "white" light. A suitable flashlamp system for use with the present embodiment is readily available as Model No. PBS-1 or PBS-2 from Pure Pulse Technologies of San Diego, Calif., which model utilizes flashlamps, such as are, for example, available as Part No. 01812-525 from PurePulse Technologies, Inc. of San Diego, Calif. The emitted light pulses have wavelengths of from the far ultraviolet (200–300 nm), through the near ultraviolet (300–380 nm), and visible (380–780 nm), to the infrared (780–1100 nm). Approximately 25% of the energy distribution is ultraviolet, 45% of the energy distribution is visible, and 30% of the energy distribution of the light is infrared. Because only one to a few, i.e., 1–3, flashes of light are required to achieve microbial deactivation, and can be delivered in a very short period of time, this process can be administered very rapidly, and is usable in high throughput applications.

The light is in the wavelength range classically known as non-ionizing wavelengths, and does not penetrate opaque materials, but is transmitted through many packaging materials and therefore may be used to treat products while in the parenteral and enteral packages described above. The primary effects of treatment, and the main anti-microbial mechanisms, are believed to relate to the rich content of broad spectrum ultraviolet light, and the very high-intensity, short-duration nature of the pulses.

Figure 11:
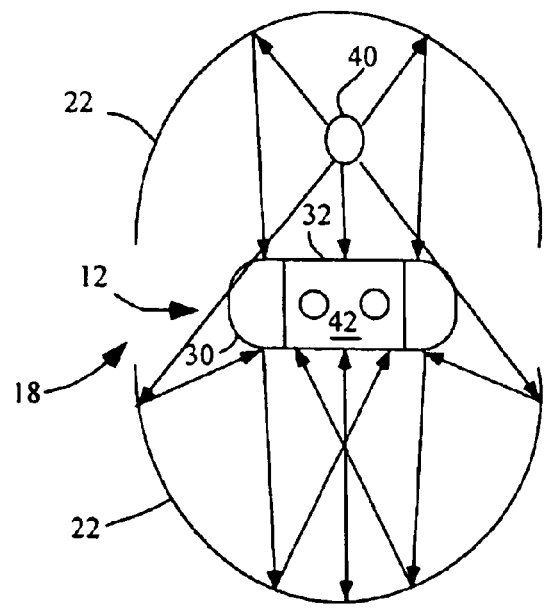
FIG. 11 is an end view of the parenteral package of FIG. 4 and another variation of the sterilizing chamber (or tunnel) of the apparatus of FIG. 3.

Referring next to FIG. 11, an end view is shown of the parenteral package of FIG. 4 in another variation of the sterilizing chamber 18 (or tunnel) of the apparatus FIG. 3. In the variation shown, a pair of reflectors 22 are positioned around one or more flashlamps 40 and the parenteral container 12, so as to form a tunnel, as the parenteral container is passed through the sterilizing chamber 18 on, for example, a conveyor belt (not shown). The variation shown functions in a manner similar to that in which variation of FIG. 7 functions except that light passing through, or passing by the parenteral container 12 after being emitted from the flashlamp 40, or reflected from an upper reflector 22, is reflected back toward the parenteral container 12 by a lower reflector 22. Advantageously, this variation maximizes the amount of light impinging upon the parenteral container 12, thereby maximizing the amount of light passing through the parenteral container 12 to deactivate microorganisms contained therein.

EXAMPLE 1

Flexible pouches of polyethylene are fabricated to contain 55 ml of either saline or dextrose. The flexible pouches are inoculated with 1 ml of a *Clostridium sporogenes* spore suspension (6.7 logs per ml.) or a *Bacillus pumilius* spore suspension (8.0 logs per ml.) and mixed. Inoculation control samples are collected from each bag with a sterile syringe in order to quantitate the numbers of viable inoculated spores recoverable from each bag before treatment.

The flexible pouches are then placed directly between two reflectors (such as shown in FIG. 11), forming a reflective cavity (or tunnel), and exposed to eight short-duration pulses of high-intensity, broad-spectrum, polychromatic light. After treatment, 1 ml of solution is removed from each bag and plated directly on tryptic soy agar (for the solution removed from the flexible pouches inoculated with *Clostridium sporogenes*) or standard methods agar (for the solution removed from the flexible pouches inoculated with *Bacillus pumilius*). The remainder of each flexible pouch is assayed for sterility by filtration. The experiment is repeated three times for each inoculum/solution combination (total of 12 tests: 3 saline/Clostridium; 3 dextrose/Clostridium; 3 saline/Bacillus; and 3 dextrose/Bacillus).

*Clostridium sporogene* spores are recovered from the saline filled flexible pouches before treatment at the concentration of 5 logs per ml (or 6.7 logs of spores per flexible pouch), and from the dextrose bags at 4.7 logs per ml (or 6.4 logs of spores per flexible pouch). *Bacillus pumilius* spores are recovered at the concentration of 6.5 logs per ml (or 8.2 logs of spores per flexible pouch) in the saline-filled flexible pouches, and at the concentration of 6.2 logs per ml (or 7.9 logs of spores per flexible pouch) in the dextrose solution samples before treatment. After treatment, no viable organisms are recovered from any of the samples, indicating that the treatment is capable of sterilizing the contents of parenteral pouches for each of the inoculum/solution combinations tested. Thus, EXAMPLE 1 achieves a sterility assurance level of greater than $10^{-6}$.

EXAMPLE 2

Blow/fill/sealed polyethylene containers are filled to various volumes (0.5, 5, 15, and 120 ml) with water-for-injection. *Bacillus pumilius* spores (ATCC 27142), *Bacillus subtillus* strain niger var. globigii spores (ATCC 9372), *Bacillus stearothermophilus* (AMSCO commercial preparation) and *Aspergillus niger* (ATCC 16404; containing conididiospores, hyphae and heads) are tested.

Six logs of each organism are inoculated by injection with a small gauge needle. Twelve replicate samples for each combination of organism, container volume, and treatment mode are inoculated. Two of the 12 samples serve as inoculation controls, and the small inoculation puncture is sealed directly with medical grade silicon sealant. Ten of the samples are treated with high-intensity, short-duration pulses of polychromatic light in a broad spectrum, before application of the medical grade silicon sealant in order to prevent shadowing of any sample volume by the sealant.

Two modes of treatment are tested. Containers are treated using a single lamp and reflector (such as shown in FIG. 10) illuminating each container from above with 20 flashes at 1.0 joule per centimeter squared per flash. In a second treatment mode, containers are treated in the reflective cavity (such as shown in FIG. 7) containing a single lamp with 10 flashes of similar fluence. These 0.5, 5 and 15 ml volumes are tested directly using 20, 20 and 60 ml pour plates respectively. The 120 ml volume samples are tested by filtration. In the single lamp and reflector (SLR) treatment mode, 36 of 40 *A. niger* samples are sterile, and all of the 40 *B. pumilus* spore and 40 *B. subtillus* globigii spore and *B. stearothermophilus* inoculated samples are sterile, i.e., free from viable microorganisms. All samples treated using the cavity treatment mode are sterile, i.e., no viable organisms are recovered from any of the 160 individual samples tested. These results demonstrate that treatment with high-intensity, short-duration pulses of polychromatic light in a broad spectrum can sterilize water-for-injection in polyethylene containers inoculated at the six log level with four resistant strains of microorganisms. Thus, EXAMPLE 2 also achieves a sterility assurance level of greater than $10^{-6}$.

Based on the above and numerous other examples, high-intensity, short-duration pulses of incoherent polychromatic light in a broad spectrum have been found to be effective in the sterilization or deactivation of microorganisms in or on pharmaceuticals, food and medical products and devices, and food and medical packaging (See, e.g., the ’559, ’942 and ’235 patents, previously incorporated herein by reference, and U.S. Pat. Nos. 4,464,336; and 5,489,442 (hereinafter the ’336 and ’442 patents, respectively), both of which are incorporated herein by reference as if set forth in their entirety.) High-intensity, short-duration pulses of polychromatic light in a broad spectrum can thus be used to produce an effective and efficient sterilization method for products, packages, and other target object in situations in which the high-intensity, short-duration pulses of polychromatic light in a broad spectrum can be arranged to access all important surfaces and/or volumes of such target object. (Important surfaces and being those surfaces and volumes for which deactivation of microorganisms is desired.) By properly arranging treatment methods and apparatuses, the skilled artisan can assure that the pulses of light will reach the important surfaces and/or volumes to be treated.

Furthermore, and unlike with heretofore known terminal sterilization processes such as autoclaving, key sterilization parameters can be monitored and controlled in accordance with the embodiments described herein. This monitoring and controlling of key sterilization parameters in accordance with embodiments described herein assures a high degree of quality and safety, i.e., a high degree of deactivation, on the target object before the target object is released to and used by an end user.

The sterilization parameters important to achieving sterilization are: (a) the spectral content of each flash, (b) the energy of each flash (or fluence-per-flash in joules/$cm^2$/flash), and (c) the number of flashes delivered.

The importance of the spectral content of each flash is demonstrated by results published in the ’559 patent, previously incorporated herein by reference, where it is shown that the ultraviolet content of the pulsed light is of primary importance for the strong antimicrobial effects of pulsed light treatment. This is seen in results of examples in which the ultraviolet content of the flash at wavelengths less than about 320 nm are removed by filtration of the light through a quarter-inch thick Pyrex glass filter. Although these results demonstrate that it is high levels of microbial deactivation can still be obtained when wavelengths less than about 320 nm are removed from the treatment flash, it is further seen that much higher fluences and numbers of flashes must be used for the production of deactivation effects under these reduced ultraviolet content conditions.

The importance of the energy of the flash (as distinguished from the total energy delivered over some number of flashes) is seen in the results of bacterial and/or fungal spore survival tests in which the ability of different pulsed light treatments to produce sterilization levels of deactivation is evaluated.

EXAMPLE 3

The importance of fluence-per-flash is further demonstrated in the results seen in Table 2 where the antimicrobial effects of pulsed light treatments are shown on *Aspergillus niger* (condiospores, hyphal debris, and sporangia recovered by a crude wash of a mature culture) inoculated by spraying onto the surface of white plastic packaging material. The log survival results are documented for a range of treatments (0.34, 0.53, 0.75, 1, and 1.3 J/cm$^2$ per flash) used as a single flash, or after various total numbers of flashes (and therefore various total treatment fluences). When 0.34 J/cm$^2$/flash treatment is performed, the resulting deactivation obtained is relatively constant at about 2 logs survival after about 7 flashes and through treatments ranging up to 40 flashes (40 flashes equals a total accumulated treatment fluence in excess of 13 J/cm$^2$). However, a treatment comprised of a single flash at 1.3 J/cm$^2$/flash is seen to result in no recovered viable organisms for each of three identically inoculated samples tested. Thus, again the treatment consisting of a lower fluence-per-flash, but a dramatically higher total treatment fluence is seen to be far inferior to a treatment consisting of a single flash at higher fluence-per-flash.

TABLE 2

| Total Treatment Fluence (Joules/sq cm) | Fluence Per Flash (Joules/sq cm/Flash) | | | | |
|---|---|---|---|---|---|
| | 0.3 | 0.53 | 0.75 | 1 | 1.3 |
| 1 | 3.48 | 2.23 | 1.18 | 0.48 | NS |
| 2 | 3.38 | 2.31 | | | NS |
| 4 | | 1.95 | 0.60 | 0.15 | NS |
| 6 | | | 0.74 | | |
| 7 | | | 0.50 | 0.53 | |
| 8 | 2.22 | 1.47 | | | NS |
| 12 | | 1.96 | | | NS |
| 16 | 1.68 | 1.23 | | | |
| 20 | | 1.67 | | | |
| 24 | 2.07 | | | | |
| 32 | 1.92 | | | | |
| 40 | 1.73 | | | | |

NS = No Survivors Detected

Thus, it is seen that the fluence-per-flash used for pulsed light treatment (as opposed to total treatment fluence) significantly affects an overall deactivation efficacy achieved on either bacterial or fungal spores.

The total number of flashes delivered is also of importance. At least one flash clearly must be delivered. In addition, when a product is treated in-flow, such as for the treatment of packaging in a continuous filling machine, such as shown in the '559 patent, or for the treatment of, e.g., running water, some overlapping of the treatment pulses is necessary (because of the digitized or quantitized nature of the light pulses verses the continuous nature of the medic being treated) and some minimum mean number of pulses per unit volume must be delivered and ensured to achieve a desired deactivation efficiency.

Thus, as shown above, the fluence-per-flash (or flash peak power) is important for achieving deactivation at sterilization levels during pulsed light disinfection. In many applications, the materials, methods, and geometry of the treatment arrangement can be configured to optimize and elevate the efficiency of the pulsed light process and its attendant killing effects.

An example has been reported (U.S. Pat. No. 5,451,367, hereinafter the '367 patent), wherein pulsed light treatment for sterilizing the inner surface of reflective multilayer packaging materials is optimized by choice of materials. A unique and key aspect of this patent is the ability of a reflective inner layer of multilayer packaging material to enhance the pulsed light exposure of microorganisms (and other particles) on the surface of the packaging by providing a mechanism for reflecting light onto the under or down surfaces which are not directly exposed by, and therefore are less accessible to, pulsed light in the absence of such reflective advantages.

A method of significant benefit not apparent from this earlier report (i.e., the '367 patent), and not apparent to the inventors thereof until recently, relates to the capabilities of the arrangement, materials, methods, and geometries described therein to enhance the efficiency and efficacy of the pulsed light treatment process via increases in fluence-per-flash (or flash peak power). For the specific application described in the '367 patent, i.e., the sterilization of the inner surface of reflective multilayer packaging materials, the apparatuses, materials, methods, and geometries discussed provides not only an increased exposure of the shadowed sides of microorganisms and particles, but can also produces an increase in fluence-per-flash without an attendant increase in flashlamp power. This is due to the reflective nature of the light confining cavity inherent in some of the geometries attendant to the described apparatuses, materials, methods and geometries. The microbiological benefit of this enhancement in effective fluence-per-flash is described in the discussion presented earlier.

By way of further example, a reflective cavity (such as shown in FIG. 11) constructed of a broadband reflective material and designed to contain a pulsed light source and a transmissive product within a transmissive packaging material can be used to increase the effective fluence-per-flash, and accordingly the microbial deactivation effects of pulsed light treatment. As a result of such arrangement, pulsed light not directly incident on the package is reflected and essentially "recycled" within the reflective cavity to eventually interact with the product. Similarly pulsed light passing through the package and product is reflected and "recycled" within the reflective cavity to again interact with the product. This "recycling" of the pulsed light results in a higher effective fluence-per-flash than would be observed absent the reflective cavity.

Such a reflective cavity, i.e., a reflective cavity exhibiting this "recycling" capability may have many shapes and designs. For example, the reflective cavity could be elliptical in shape with the pulsed light source located at one focus of the ellipse, and the product to be treated located at the other focus. Alternately the reflective cavity could be shaped or patterned to facilitate the return of nonabsorbed light back onto or into the product or package being treated, or to reflect varying fluence levels at various parts of the product or package being treated.

Similarly, the product or package to be treated may be of many types, shapes, materials, and designs. For example, the product may be a solution to be treated that is conveyed through the reflective pulsed light treatment chamber in flow in a light transmissive tube, or the product may be air or another gas treated in flow in a reflective pipe or duct. The product may be transmissive to all, a portion of, or none of the pulsed light treatment spectrum employed. Thus, variations on the embodiments described herein may have as their design goal the treatment of the surface of a product (such as the surface of a package), the surface of a package and the product within (such as the surface of a product enclosed within a transmissive package), or the surfaces and volume of a product (such as a transmissive package containing a transmissive product). A wide array of products and cavities are thus contemplated by the inventors named herein.

A common feature, however, of the possible shapes, designs, arrays, and configurations of products, packaging materials, devices, and treatment chambers should preferably be that the apparatuses, methods, materials, and geometries are arranged so as to provide for or permit the reflection of light not initially absorbed within the product, package, etc. in a manner such that such light can be recycled within the cavity to increase the likelihood of the light finally interacting with or being absorbed by the product or package; or microorganisms, chemicals, or contaminants on or in the product or packaging material.

The degree of success or efficiency of the recycling of the initially unabsorbed light will vary with the apparatuses, materials, methods, and geometries employed.

For example, the cavity quotient or Q (the ratio of energy loss per cycle versus the energy stored in the cavity) will vary based upon the pulsed light wavelengths employed, the reflectivity of the cavity walls, the ability of the cavity to refocus the light back to useful product surfaces or volume, etc.

However, preferably in all instances the cavity will provide an increase in fluence-per-flash and an enhancement in efficiency by providing for some reutilization of initially unabsorbed light.

For a package and/or product and treatment chamber design that are such that pulsed light within the particular frequency spectrum used for sterilization can reach all the important volumes and surfaces, pulsed light sterilization is dependent upon the spectral content of each flash, the energy of each flash (or fluence-per-flash in Joules/$cm^2$/f lash), and the number of flashes delivered. Advantageously, these three parameters are relatively easily and reliably measurable during pulsed light treatment. These three parameters, in accordance with the present embodiments are monitored, controlled, and verified during pulsed light treatment operations. This monitoring, controlling, and verifying proper treatment can then be used for validation of the treatment, i.e., verification that sufficient deactivation is achieved. Specifically, such monitoring, controlling and verifying of proper treatment allows validation of treatment based on measurements of these three parameters alone, as opposed to observation of the packages or products treated for microbial activity following a waiting period.

A key advantage to the use of pulsed light is thus the ability to monitor, control and verify the key treatment parameters, and hence the sterilization effect, in real time and for each package. This importance, i.e., the importance of the ability to control, monitor and verify a sterilization technology, will be appreciated by those familiar with the use and acceptance of sterilization techniques.

Instantaneous, on-line monitoring and evaluation of each flash of the pulsed light treatment process can be performed at the product, the packaging material, the device or other target object. For transmissive products and packages, the light going through the product and package can be measured both for fluence-per-flash (or flash peak power) and for spectral content. For products and packages that are not transmissive in the wavelengths of interest, reflection off of the product or package can be similarly measured. In both instances the measurement can be performed at one or a multiplicity of sites, or alternatively in a volumetric mode where a large area or volume of the product or package illumination area or volume is sampled through the use of lenses or other mechanisms capable of collecting light over a large angle. In this way pulsed light treatment can be favorably monitored, controlled (through appropriate closed loop feedback control systems), and verified. Thus, not only can each treatment flash be sampled and confirmed as having a minimally sufficient fluence-per-flash and minimally sufficient spectral content, but the fluence-per-flash and spectral content of the light received by the product or package is also monitored in accordance with the present embodiments. This monitoring is performed in an instantaneous, on-line fashion permitting the highest levels of parametric control and verification.

Figure 12:
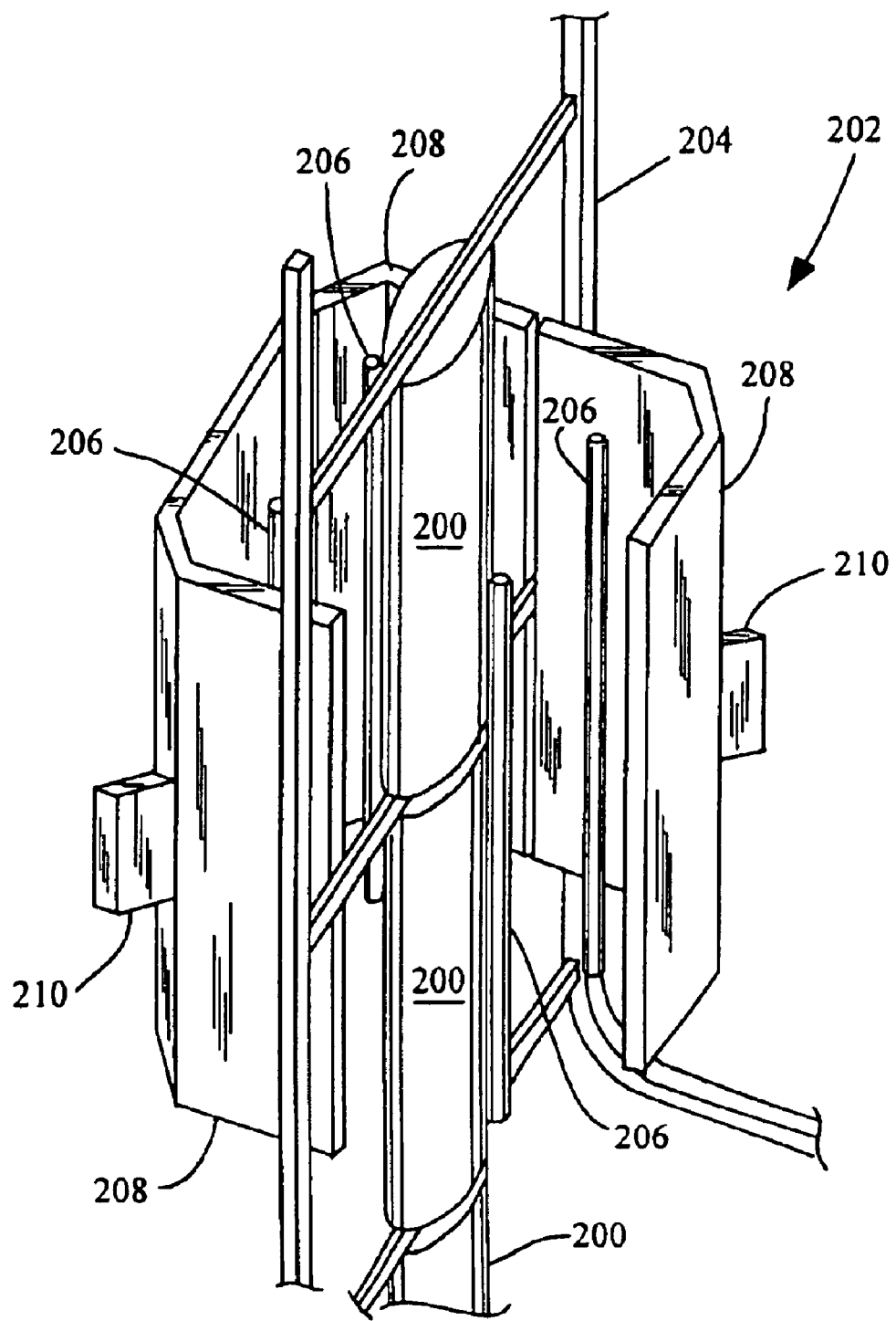
FIG. 12 is a perspective view of several parenteral packages, a further variation of the sterilization chamber (or tunnel) of the apparatus of FIG. 3, and a transport approach for moving the parenteral packages through the sterilization chamber.

Referring to FIG. 12, a perspective view is shown of several parenteral packages 200, a further variation of the treatment chamber 202 (or tunnel), and a transport approach for moving the parenteral packages through the sterilization chamber. The parenteral packages 200 (IV bags), such as the type used to hold intravenous (IV) and parenteral solutions, are treated by hanging them on a ladder-like transport mechanism 204 that carries them vertically through the treatment chamber 202. Pairs of flashlamps 206 are located on each side of the packages 200 as they move through the treatment chamber 202. The treatment chamber 206 includes the flashlamps 206 and reflectors 208 that project light onto the parenteral packages 200. The shape of the reflector 208 are controlled to establish distribution of light as required by the parenteral package 200, i.e., to distribute light onto the parenteral packages 200 such that sufficient fluence-per-flash is directed to each unit volume of the parenteral package 200 and product therein to effect deactivation of microorganisms. The reflectors 208 also increase the Q (the ratio of the energy stored in the cavity versus the energy lost per cycle) of the treatment chamber 202 and allow multiple bounces of light, thus increasing the efficiency and efficacy of the treatment chamber 202. Also shown are photodetectors 210 or other detectors that provide monitoring, control, and verification of the treatment process. Not shown are monitoring and control circuitry and a computer also for monitoring, control and verification.

Pulsed light sterilization of IV bags 200 or parenteral solutions may require attention to design, materials and their thickness and other key parameters to assure light can reach and hence sterilize all the important volume and surfaces of the product. Particular attention may have to be paid to special features such as fitments and other normal components on or to the bag which because of stiffness requirements or other considerations may necessitate design or materials selection specifically suited for use with pulsed light while still meeting stiffness requirements, etc.

Another method of treating products is to lay them on a conveyor, such as is illustrated in FIG. 3. A section of the conveyor is preferably transparent and in this area packages are treated from the top and the bottom to provide complete coverage.

Figure 13:
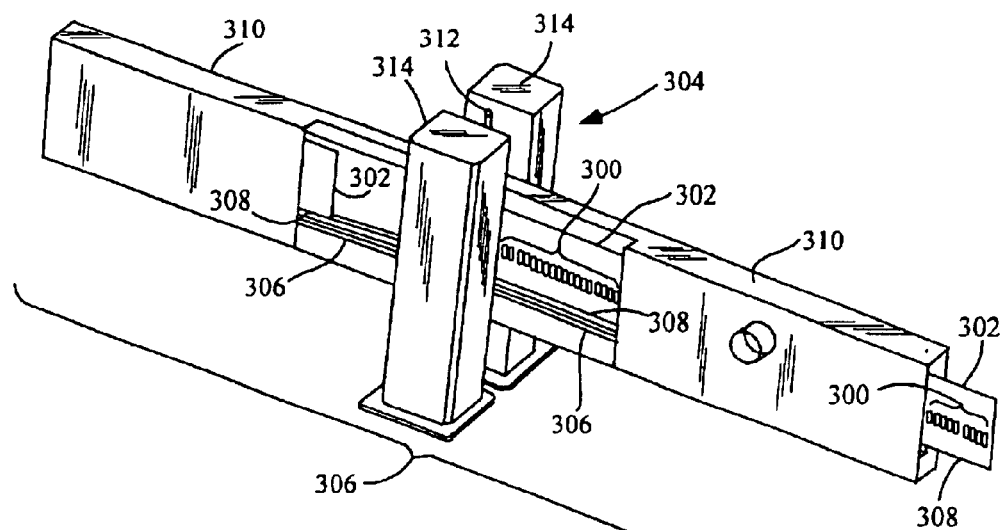
FIG. 13 is a perspective view of several blow-fill-seal containers on several cards, an additional variation of the sterilization chamber (or tunnel) of the apparatus of FIG. 3, and a transport approach for moving the cards through the sterilization chamber.

FIG. 13 is a perspective view of several blow-molded containers 300 on several cards 302, an additional variation of the treatment chamber 304 (or tunnel), and a transport approach 306 for moving the cards 302 through the treatment chamber 304. Also present, but not shown, are photodetectors or other detectors that provide monitoring control, and verification of the treatment process. Monitoring and control circuit (not shown) and a computer (not shown) are also used for monitoring control and verification.

The blow molded packages 300 that are grouped into the cards 302 and are transported on a conveyor such as Model No. 624-44066 produced by Wyler Engineering of Elk Grove, Ill. These conveyors use a round elastomer belt 306 to carry the cards 302. A plastic flashing 308 on the cards supports the cards on the round elastomer belt 306.

In operation, the cards 302 enter the treatment chamber 304 through a tunnel 310. The tunnel 310 is designed to contain pulses of light produced by flashlamps 312 so as to protect operators. A photoeye (not shown) is used to detect the presence of a card 302 in response to which the pulses of light are initiated automatically, preferably after a delay to assure that the card 302 is in proper position for treatment. The flashlamps 312 are located within reflector housings 314 on both sides of the cards 302 to assure complete treatment. The flashlamps 312 are fired simultaneously to maximize fluence-per-flash for increased sterilization effectivity as illustrated in the examples above.

Figure 14:
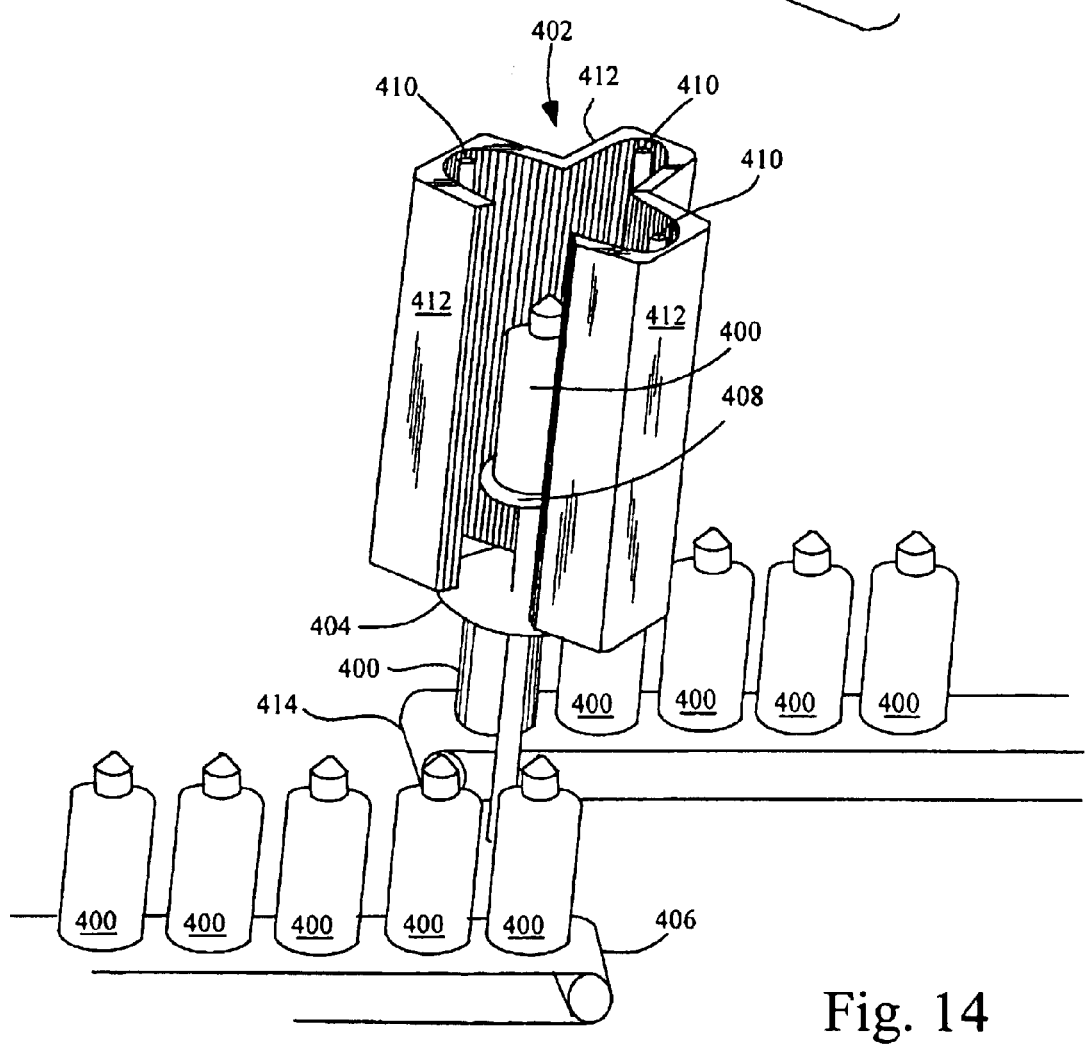
FIG. 14 is a perspective view of several enteral packages, a further additional variation of the sterilization chamber of the apparatus of FIG. 3, and a transport approach for moving the enteral packages through the sterilization chamber.

Referring to FIG. 14, a perspective view is shown of several enteral packages 400 (or other packages that stand erect), a further additional variation of the treatment chamber 402, and a transport apparatus 404 for moving the enteral packages 400 through the treatment chamber 402. Also present, but not shown, are photodetectors or other detectors that provide monitoring control, and verification of the treatment process. Monitoring and control circuit (not shown) and a computer (not shown) are also used for monitoring control and verification.

The enteral packages 400 are carried on a first conveyor 406 to the treatment chamber 402. A transfer device (not shown) moves the enteral packages over by one off the first conveyor 406 onto a platform 408. The platform 408 moves the enteral packages 400 up and into the treatment chamber 402. The treatment chamber 402 includes four flashlamps 410 and four corresponding reflectors 412 (one of each of which have been omitted from FIG. 12 to permit viewing of the enteral package 400 on the platform 408) arranged in what is roughly quadracylindrical arrangement, i.e., four elongated bulbous lobes arranged with adjacent edges juxtaposed against one another. All of the flashlamps 40 are preferably flashed simultaneously in order to maximize fluence-per-flash and thus deactivation of microorganisms. Also, the reflectors 412 are designed to form a high Q treatment chamber 402, and thus to make maximum usage of the pulses of light emitted from the flashlamps. Following one or more flashes of the flashlamp 410, the platform 40 is lowered and a new enteral package 400 is moved into place by the transport mechanism (not shown), as the initial enteral package 400 is moved onto a second conveyor 414.

While the invention herein disclosed has been described by means of specific embodiments and applications thereof, numerous modifications and variations could be made thereto by those skilled in the art without departing from the scope of the invention set forth in the claims.

What is claimed is:

1. An apparatus for sterilizing microorganisms in a container comprising:
   the container, wherein the container includes a blister formed therein;
   a backing material that together with the blister form a cavity in which is contained a contact lens and a preservative fluid;
   a flashlamp for generating high-intensity, short-duration pulses of light, and for deactivating microorganisms within the container by illuminating the container with the pulses of light having been generated.

2. The apparatus of claim 1 wherein said sealed contact lens container includes a polyolefin.

3. The apparatus of claim 1 wherein said sealed contact lens container includes polyethylene.

4. The apparatus of claim 1 wherein said sealed contact lens container transmits light in a spectrum of from between 180 nm and 300 nm.

5. The apparatus of claim 1 wherein said preservative fluid is at least one percent transmissive to light having a wavelength of 260 nanometers.

6. The apparatus of claim 1 wherein said flashlamp deactivating includes means for achieving a sterility assurance level of at least $10^{-6}$.

7. The apparatus of claim 1 wherein said flashlamp generates high-intensity, short-duration pulses of polychromatic light.

8. An apparatus for deactivating microorganisms in a container comprising:
   a sealed contact lens container;
   a preservative fluid and a contact lens within the sealed contact lens container; and
   a flashlamp for generating pulses of light, portions of which transmit through at least a portion of the sealed contact lens container and deactivate microorganisms on the contact lens.

9. The apparatus of claim 8 wherein the flashlamp generates pulses of polychromatic light.

10. The apparatus of claim 8 wherein at least a portion of the sealed contact lens container is transmissive to light having wavelengths at least between 180 and 300 nm.

11. The apparatus of claim 8 wherein each of the pulses of light has an intensity of at least about $0.01$ $J/cm^2$.

12. The apparatus of claim 8 wherein at least about 1% of pulses of light has a wavelength at about 260 nm.

13. An apparatus for deactivating microorganisms in a container comprising:
   a sealed contact lens container;
   a preservative fluid and a contact lens within the sealed contact lens container; and
   a lamp for generating light having an energy density at least about $2.5$ $mJ/cm^2$ at wavelengths between 200 and 380 nm, wherein at least a portion of the light transmits through at least a portion of the sealed contact lens container and deactivates microorganisms on the contact lens.

14. The apparatus of claim 13 wherein the lamp comprises a flashlamp for generating one or more pulses of light.

15. The apparatus of claim 13 wherein the lamp generates light having an energy density at least about $0.18$ $mJ/cm^2$ at wavelengths between 240 and 280 nm.

16. An apparatus comprising:
   a sealed contact lens container containing a preservative fluid and a contact lens wherein at least a portion of the sealed contact lens container is transmissive to light having wavelengths at least between about 180 and about 300 nm; and
   a light source for generating light, at least portions of which transmit through at least a portion of the sealed contact lens container and deactivate microorganisms on the contact lens.

17. The apparatus of claim 16 wherein the sealed contact lens container includes:
   a blister formed therein;
   a backing material that together with the blister form a cavity in which is contained the contact lens and the preservative fluid.

18. The apparatus of claim 16 wherein the light source generates pulses of light.

19. The apparatus of claim 16 wherein the light source generates pulses of polychromatic light.

20. The apparatus of claim 16 wherein at least a portion of the sealed contact lens container is transmissive to light having wavelengths at least between about 180 and about 300 nm.

21. The apparatus of claim 16 wherein the light has an intensity of at least about 0.01 J/cm$^2$.

22. The apparatus of claim 16 wherein at least about 1% of the light has a wavelength of about 260 nm.

23. A method of deactivating microorganisms comprising:
illuminating a sealed contact lens container with light, wherein at least a portion of the sealed contact lens container is transmissive to at least a portion of the light, the sealed contact lens container containing a preservative fluid and a contact lens; and
deactivating microorganisms on the contact lens within the sealed contact lens container.

24. The method of claim 23 further comprising deactivating microorganisms within the preservative fluid within the sealed contact lens container.

25. The method of claim 23 wherein the illuminating step comprises illuminating the sealed contact lens container with one or more pulses of light.

26. The method of claim 23 wherein the illuminating step comprises illuminating the sealed contact lens container with one or more pulses of polychromatic light.

27. The method of claim 23 wherein the illuminating step comprises illuminating the sealed contact lens container with one or more pulses of light having a wavelength of about 260 nm, wherein at least a portion of the sealed contact lens container is transmissive to at least a portion of the light having the wavelength of about 260 nm.

28. The method of claim 23 wherein the illuminating step comprises illuminating the sealed contact lens container with one or more pulses of light having wavelengths between about 180 and about 300 nm, wherein at least a portion of the sealed contact lens container is transmissive to at least a portion of the one or more pulses of light having the wavelengths between about 180 and about 300 nm.

29. The method of claim 23 wherein the illuminating step comprises illuminating the sealed contact lens container with one or more pulses of far UV light, wherein at least a portion of the sealed contact lens container is transmissive to at least a portion of the far UV light.

30. A method comprising:
providing a sealed contact lens container including a blister formed therein and including a backing material that together with the blister form a cavity in which is contained a preservative fluid and a contact lens; and
illuminating the contact lens with one or more pulses of light in order to deactivate microorganisms on the contact lens.

31. A method comprising:
providing a sealed contact lens container containing a preservative fluid and a contact lens; and
illuminating the contact lens with light in order to deactivate microorganisms on the contact lens comprising transmitting at least a portion of the light through at least a portion of the sealed contact lens container to illuminate the contact lens.

32. The method of claim 31 further comprising transmitting at least a portion of the light through at least a portion of the sealed contact lens container to illuminate the contact lens.

33. The method of claim 31 wherein the illuminating step comprises illuminating the contact lens with one or more pulses of light.

34. The method of claim 31 wherein the illuminating step comprises illuminating the contact lens with one or more pulses of polychromatic light.

35. The method of claim 31 wherein the illuminating step comprises illuminating the contact lens with one or more pulses of polychromatic light having wavelengths within a range of about 180 to about 300 nm.

36. The method of claim 31 wherein the illuminating step comprises illuminating the contact lens with one or more pulses of polychromatic light such that at least 1% of the one or more pulses of polychromatic light at a wavelength of 260 nm reaches the contact lens.

37. The method of claim 31 wherein illuminating step comprises illuminating the contact lens with the light for achieving a sterility assurance level of at least $10^{-6}$.

* * * * *